United States Patent
Lin et al.

(10) Patent No.: US 11,993,782 B2
(45) Date of Patent: May 28, 2024

(54) LENTIVIRUS PACKAGING SYSTEM, LENTIVIRUS PRODUCED BY THE SAME, CELL TRANSDUCED BY THE LENTIVIRUS, METHOD FOR IMPROVING LENTIVIRUS PRODUCTION IN A HOST CELL, AND METHOD OF USING THE CELL FOR TREATING CANCER

(71) Applicant: PELL BIO-MED TECHNOLOGY CO., LTD., Taipei (TW)

(72) Inventors: Wei-Chi Lin, Taipei (TW); Ssu-Yu Chou, Taipei (TW); Yao-Cheng Yang, Taipei (TW); Chien-Ting Lin, Taipei (TW); Chen-Lung Lin, Kaohsiung (TW)

(73) Assignee: PELL BIO-MED TECHNOLOGY CO., LTD., Taipei (TW)

( * ) Notice: Subject to any disclaimer, the term of this patent is extended or adjusted under 35 U.S.C. 154(b) by 0 days.

(21) Appl. No.: 17/377,830

(22) Filed: Jul. 16, 2021

(65) Prior Publication Data

US 2022/0348956 A1  Nov. 3, 2022

(30) Foreign Application Priority Data

Apr. 28, 2021 (TW) ................. 110115343

(51) Int. Cl.
*C12N 15/86* (2006.01)
*A61K 35/17* (2015.01)
(Continued)

(52) U.S. Cl.
CPC .............. *C12N 15/86* (2013.01); *A61K 35/17* (2013.01); *C07K 14/70503* (2013.01); *C12N 7/00* (2013.01); *C12N 2740/15043* (2013.01)

(58) Field of Classification Search
CPC ................... C12N 15/86; C12N 7/00; C12N 2740/15043; A61K 35/17; C07K 14/70503
See application file for complete search history.

(56) References Cited

U.S. PATENT DOCUMENTS

| 6,063,612 A * | 5/2000 | Jayasena ............... C12N 15/113 |
| | | 435/235.1 |
| 2003/0039636 A1 | 2/2003 | Leboulch |
| 2015/0283266 A1 | 10/2015 | Anderson |

FOREIGN PATENT DOCUMENTS

| CN | 108114276 A | 6/2018 |
| CN | 112011574 A | 12/2020 |

(Continued)

OTHER PUBLICATIONS

Dull et al. A Third-Generation Lentivirus Vector with a Conditional Packaging System. Journal of Virology. 1998; 8463-8471. (Year: 1998).*

(Continued)

*Primary Examiner* — Arthur S Leonard
*Assistant Examiner* — Jianjian Zhu
(74) *Attorney, Agent, or Firm* — WPAT, PC

(57) ABSTRACT

Provided is a lentivirus packaging system, which comprises: a transfer plasmid comprising a nucleotide sequence of TAR-reserved-chimeric 5' long terminal repeat (LTR); at least one packaging plasmid comprising a nucleotide sequence encoding TAR RNA binding protein, a nucleotide sequence of rev gene, a nucleotide sequence of gag gene, and a nucleotide sequence of pol gene; and an envelope plasmid. Due to the expression of gene of TAR RNA binding protein by the packaging plasmids, the produced lentivirus has higher virus titer and can improve the transduction rate and the gene delivery efficiency during cell transduction. The present invention further provides a method of improving lentivirus production in a host cell, which comprises (Continued)

using the lentivirus packaging system to transfect the host cell. The present invention further provides a cell transduced by the lentivirus and a method of using the cell for treating cancer.

9 Claims, 8 Drawing Sheets

Specification includes a Sequence Listing.

(51) Int. Cl.
    *C07K 14/705*     (2006.01)
    *C12N 7/00*     (2006.01)

(56) References Cited

FOREIGN PATENT DOCUMENTS

| | | |
|---|---|---|
| JP | 2008538174 A | 10/2008 |
| JP | 2013059331 A | 4/2013 |
| JP | 2020188777 A | 11/2020 |
| WO | WO 00/00600 A2 | 1/2000 |
| WO | WO0066759 A1 | 11/2000 |
| WO | WO 2006/089001 A2 | 8/2006 |
| WO | WO2006090906 A1 | 8/2006 |
| WO | WO2010/070094 A1 | 6/2010 |
| WO | WO2014092090 A1 | 6/2014 |
| WO | WO2014092094 A1 | 6/2014 |
| WO | WO2020059848 A1 | 3/2020 |
| WO | WO2020113037 A1 | 6/2020 |

OTHER PUBLICATIONS

Zufferey et al. Multiply attenuated lentiviral vector achieves efficient gene delivery in vivo. Nature Biotechnology. 1997; 15:871-875. (Year: 1997).*

SCORE sequence comparison result and archived webpage of Addgene for pCMV-dR8.91. downloaded from https://web.archive.org/web/20150208124731/http://www.addgene.org/vector-database/2221/ downloaded on Feb. 20, 2023. (Year: 2023).*

European Patent Office, Extended European search report issued on Feb. 21, 2022(EP21189281.5).

Peirong Hu et al., Superior lentiviral vectors designed for BSL-0 environment abolish vector mobilization, Sep. 6, 2018, Springer Nature Limited.

V. Narry Kim et al., Minimal requirement for a lentivirus vector based on human immunodeficiency virus type 1, Journal of Virology, Jan. 1998;72(1):811-6.

Japan Patent Office, Office action issued on Oct. 25, 2022(JP2021142315).

Taiwan Patent Office, Office Action issued on Oct. 20, 2021(TW110115343).

Addgene, Lentiviral Guide, 2011.

Ying Poi Liu et al., HIV-1-Based Lentiviral Vectors, 2014, Springer Science+Business Media, LLC.

Australia Patent Office, Examination report issued on Feb. 6, 2023 (AU2021206846).

V. Narry Kim et al., Minimal Requirement for a Lentivirus Vector Based on Human Immunodeficiency Virus Type 1, Journal of virology, 1997.

Stéphanie Durand et al., The Inside Out of Lentiviral Vectors, Viruses, Feb. 14, 2011.

Gilles Pernod et al., Increasing lentiviral vector titer using inhibitors of protein kinase R, BioTechniques, Apr. 2004.

China Patent Office, Office Action issued on Nov. 20, 2023 (CN202110465505.5).

Taiwan Patent Office, Office Action issued on Jun. 7, 2023(TW111107832).

Japan Patent Office, Final Rejection issued on Aug. 1, 2023(JP2021142315).

* cited by examiner

SEQUENCE LISTING

```
<160> NUMBER OF SEQ ID NOS: 3

<210> SEQ ID NO 1
<211> LENGTH: 261
<212> TYPE: DNA
<213> ORGANISM: Artificial Sequence
<220> FEATURE:
```

-continued

```
<223> OTHER INFORMATION: synthesized sequence; tat gene without introns

<400> SEQUENCE: 1
atggagccag tagatcctag actagagccc tggaagcatc caggaagtca gcctaaaact      60
gcttgtacca attgctattg taaaaagtgt tgctttcatt gccaagtttg tttcatgaca     120
aaagccttag gcatctccta tggcaggaag aagcggagac agcgacgaag agctcatcag     180
aacagtcaga ctcatcaagc ttctctatca aagcagccca cctcccaacc ccgaggggac     240
ccgacaggcc cgaaggaata a                                               261

<210> SEQ ID NO 2
<211> LENGTH: 57
<212> TYPE: DNA
<213> ORGANISM: Human immunodeficiency virus type 1
<220> FEATURE:
<223> OTHER INFORMATION: the nucleic acid sequence encoding TAR in
      TAR-reserved chimeric 5'-LTR

<400> SEQUENCE: 2
ggtctctctg gttagaccag atctgagcct gggagctctc tggctaacta gagaacc          57

<210> SEQ ID NO 3
<211> LENGTH: 20
<212> TYPE: RNA
<213> ORGANISM: Artificial Sequence
<220> FEATURE:
<223> OTHER INFORMATION: synthesized sequence; gRNA targeting pkr
      genomic sequence

<400> SEQUENCE: 3
gcaaccuacc uccuaucaug                                                  20
```

LENTIVIRUS PACKAGING SYSTEM, LENTIVIRUS PRODUCED BY THE SAME, CELL TRANSDUCED BY THE LENTIVIRUS, METHOD FOR IMPROVING LENTIVIRUS PRODUCTION IN A HOST CELL, AND METHOD OF USING THE CELL FOR TREATING CANCER

CROSS-REFERENCE TO RELATED APPLICATION

Pursuant to 35 U.S.C. § 119(a), this application claims the benefits of the priority to Taiwan Patent Application No. 110115343, filed on Apr. 28, 2021. The contents of the prior application are incorporated herein by its entirety.

BACKGROUND OF THE INVENTION

1. Field of the Invention

The present invention relates to a lentivirus packaging system, especially a lentivirus packaging system comprising a plasmid comprising a nucleotide sequence encoding TAR RNA binding protein and a plasmid comprising a nucleotide sequence of TAR-reserved chimeric 5'-long terminal repeat (LTR).

Lentivirus, a kind of retrovirus, is widely used in delivering a gene of interest into hard-to-transfect cells, for example, primary T cells. Unlike other retroviruses, lentivirus can transduce both dividing and non-dividing cells, and can infect cells of different origins by using the combination of lentivirus and VSVG protein. Besides, the RNA genome capacity of lentivirus is about 10 Kb, which is more flexible for delivering a larger or more complicated gene sequence. All these advantages of lentivirus make it widely applied on clinical treatment.

To produce lentivirus, the transfer plasmid, which comprises a gene of interest, and other plasmids, which comprise viral genes required for lentivirus packaging, are co-transduced into 293T cells. After plasmid transfection, lentivirus particles comprising the gene sequence of interest will be released into a culture medium. The culture medium will be harvested later and the lentivirus particles will be concentrated, then formulated to the concentration ready for use and stored at −80° C.

Over the past decades, the lentivirus packaging system has developed constantly. The first-generation lentivirus packaging system at the very beginning involves three plasmids, including a transfer plasmid, a plasmid that can express an envelop protein, and a plasmid comprising both essential HIV-1 viral genes (gag, pol, tat and rev) and several accessory genes (vif, vpu, vpr and nef). The viral gag gene encodes several viral capsid proteins, and the viral pol gene encodes reverse transcriptase, integrase and protease that are important for virus packaging and infection. As the four accessory genes are neither necessary for lentivirus packaging nor required for target cell infection, they were removed from the second-generation lentivirus packaging system. In the first- and second-generation lentivirus packaging systems, the transcription of viral genome comprising the gene of interest in the transfer plasmid is driven by both the 5' long terminal repeat (LTR), which serves as a promoter, and TAT protein, a kind of trans-activating regulatory protein that can bind to the trans-activation response (TAR) sequence in the LTR.

For the third-generation lentivirus packaging system, in order to further improve the safety of lentivirus, especially to avoid the development of replication competent lentivirus, the 5' and 3' LTR flanking the gene of interest were modified and the rev gene was moved to a fourth plasmid to further reduce the chance of sequence recombination. Accordingly, the modified LTR no longer retained the promoter activity, and the transcription of viral genome sequence on the transfer plasmid was instead driven by a Rous sarcoma virus (RSV) promoter or a cytomegalovirus (CMV) promoter positioned in front of the modified 5' LTR. Furthermore, the tat gene was considered useless and removed from the third-generation lentivirus packaging system to enhance the transduction efficiency of the lentivirus packaging system.

However, compared with the second-generation lentivirus packaging system, the third-generation lentivirus packaging system compromised its lentiviral yield significantly to become safer for clinical application, so there is a strong demand for a lentivirus packaging system with improved lentivirus production efficiency.

SUMMARY OF THE INVENTION

To overcome the deficit in current technology, the objective of the present invention is to increase lentivirus yield of the third-generation lentivirus packaging system without compromising the safety thereof.

To achieve the aforementioned objective, the present invention provides a lentivirus packaging system, comprising a transfer plasmid comprising a nucleotide sequence of trans-activation response (TAR) element-reserved chimeric 5' long terminal repeat (TAR-reserved chimeric 5'-LTR); at least one packaging plasmid comprising a nucleotide sequence encoding TAR RNA binding protein, a nucleotide sequence of rev gene, a nucleotide sequence of gag gene and a nucleotide sequence of pol gene; and an envelope plasmid.

By adding a plasmid comprising a nucleotide sequence encoding TAR RNA binding protein into the third-generation lentivirus packaging system, the present invention increases the yield of lentivirus, the virus titer, especially the functional titer, and the gene delivery efficiency of the produced lentivirus during transduction.

Preferably, the nucleotide sequence encoding TAR RNA binding protein is a nucleotide sequence of tat gene.

Preferably, the nucleotide sequence of tat gene comprises a nucleotide sequence of SEQ ID NO: 1, which is at least a part of the gene of TAR RNA binding protein. Furthermore, the nucleotide sequence of SEQ ID NO: 1 has no introns, which is smaller in plasmid size and different from the nucleotide sequence of tat gene commonly used in the second-generation lentivirus packaging system.

Preferably, the nucleotide sequence of TAR-reserved chimeric 5'-LTR contains a nucleotide sequence of TAR, which comprises a nucleotide sequence of SEQ ID NO: 2.

Preferably, the 5' LTR in the nucleotide sequence of TAR-reserved chimeric 5'-LTR has a U3 region, which is truncated and replaced with an RSV promoter or a CMV promoter to prevent the virus from constant replication and enhance safety. Additionally, the nucleotide sequence of TAR-reserved chimeric 5'-LTR is the same as that in the third-generation lentivirus packaging system. In one embodiment of the present invention, the RSV promoter is adopted to drive the transcription.

Preferably, the number of the at least one packaging plasmid is equal to the total number of the nucleotide sequence encoding TAR RNA binding protein, the nucleotide sequence of rev gene, the nucleotide sequence of gag gene and the nucleotide sequence of pol gene. For example, when the number of each of the nucleotide sequence encoding TAR RNA binding protein, the nucleotide sequence of rev gene, the nucleotide sequence of gag gene and the nucleotide sequence of pol gene is one, namely four nucleotide sequences in total, the number of plasmids is also four in total, which means the at least one packaging plasmid comprises a first packaging plasmid, a second packaging plasmid, a third packaging plasmid and a fourth packaging plasmid, wherein the first packaging plasmid comprises the nucleotide sequence encoding TAR RNA binding protein, the second packaging plasmid comprises the nucleotide sequence of rev gene, the third packaging plasmid comprises the nucleotide sequence of gag gene, and the fourth packaging plasmid comprises the nucleotide sequence of pol gene. Preferably, the at least one packaging plasmid each comprises one respective nucleotide sequence, which is different from each other.

Preferably, the at least one packaging plasmid comprises a first packaging plasmid and a second packaging plasmid, and the first packaging plasmid comprises one of the nucleotide sequence encoding TAR RNA binding protein, the nucleotide sequence of rev gene, the nucleotide sequence of gag gene and the nucleotide sequence of pol gene, and the second packaging plasmid comprises the rest of the nucleotide sequence of gene of TAR RNA binding protein, the nucleotide sequence of rev gene, the nucleotide sequence of gag gene and the nucleotide sequence of pol gene. For example, the first packaging plasmid comprises the nucleotide sequence encoding TAR RNA binding protein, and the second packaging plasmid comprises the nucleotide sequence of rev gene, the nucleotide sequence of gag gene and the nucleotide sequence of pol gene. Alternatively, the first packaging plasmid comprises the nucleotide sequence of rev gene, and the second packaging plasmid comprises the nucleotide sequence encoding TAR RNA binding protein, the nucleotide sequence of gag gene and the nucleotide sequence of pol gene.

Preferably, the at least one packaging plasmid comprises a first packaging plasmid and a second packaging plasmid, and the first packaging plasmid comprises two of the nucleotide sequence encoding TAR RNA binding protein, the nucleotide sequence of rev gene, the nucleotide sequence of gag gene and the nucleotide sequence of pol gene, and the second packaging plasmid comprises the rest of the nucleotide sequence encoding TAR RNA binding protein, the nucleotide sequence of rev gene, the nucleotide sequence of gag gene and the nucleotide sequence of pol gene. Furthermore, each of the nucleotide sequences in the first packaging plasmid is different from each of those in the second packaging plasmid. For example, the first packaging plasmid comprises the nucleotide sequence encoding TAR RNA binding protein and the nucleotide sequence of gag gene, and the second packaging plasmid comprises the nucleotide sequence of rev gene and the nucleotide sequence of pol gene. Alternatively, the first packaging plasmid comprises the nucleotide sequence encoding TAR RNA binding protein and the nucleotide sequence of pol gene, and the second packaging plasmid comprises the nucleotide sequence of rev gene and the nucleotide sequence of gag gene.

Preferably, the at least one packaging plasmid comprises a first packaging plasmid, a second packaging plasmid and a third packaging plasmid, wherein the first packaging plasmid comprises two of the nucleotide sequence encoding TAR RNA binding protein, the nucleotide sequence of rev gene, the nucleotide sequence of gag gene and the nucleotide sequence of pol gene, and the second packaging plasmid and the third packaging plasmid each comprises one of the rest of the nucleotide sequence encoding TAR RNA binding protein, the nucleotide sequence of rev gene, the nucleotide sequence of gag gene and the nucleotide sequence of pol gene. Furthermore, the nucleotide sequences contained in the first packaging plasmid, in the second packaging plasmid and in the third packaging plasmid are different from each other. In other words, the second packaging plasmid and the third packaging plasmid each comprise a respective one of the other two of the nucleotide sequence encoding TAR RNA binding protein, the nucleotide sequence of rev gene, the nucleotide sequence of gag gene and the nucleotide sequence of pol gene. In one embodiment, the first packaging plasmid comprises the nucleotide sequence of gag gene and the nucleotide sequence of pol gene, the second packaging plasmid comprises the nucleotide sequence encoding TAR RNA binding protein, and the third packaging plasmid comprises the nucleotide sequence of rev gene. In such embodiment, the yield of lentivirus will not decrease due to the increased number of plasmids during co-transfection, but on the contrary, will be higher than that of the third-generation lentivirus packaging system comprising less number of plasmids.

Preferably, a weight ratio of the transfer plasmid, the first packaging plasmid, the second packaging plasmid, the third packaging plasmid and the envelope plasmid is 3 to 12:3 to 7:1 to 4:1 to 4:0.8 to 6. More preferably, the weight ratio of the transfer plasmid, the first packaging plasmid, the second packaging plasmid, the third packaging plasmid and the envelope plasmid is 4 to 11:4 to 7:1.5 to 3.5:1.5 to 3.5:0.9 to 4.5. At such weight ratio, more lentivirus can be produced.

In one embodiment, the weight ratio of the transfer plasmid, the first packaging plasmid, the second packaging plasmid, the third packaging plasmid and the envelope plasmid is 4.5 to 5.5:4.5 to 5.5:1.5 to 2.5:1.5 to 2.5:3.5 to 4.5. At such weight ratio, more lentivirus can be produced. Preferably, the weight ratio of the transfer plasmid, the first packaging plasmid, the second packaging plasmid, the third packaging plasmid and the envelope plasmid is 5:5:2:2:4. At such weight ratio, more lentivirus can be produced.

In one embodiment, the weight ratio of the transfer plasmid, the first packaging plasmid, the second packaging plasmid, the third packaging plasmid and the envelope plasmid is 9.5 to 10.5:5.5 to 6.5:2.5 to 3.5:2.5 to 3.5:0.9 to 1.1. At such weight ratio, more lentivirus can be produced. Preferably, the weight ratio of the transfer plasmid, the first packaging plasmid, the second packaging plasmid, the third packaging plasmid and the envelope plasmid is 10:6:3:3:1. At such weight ratio, more lentivirus can be produced.

Preferably, the envelope plasmid comprises a nucleotide sequence encoding vesicular stomatitis virus glycoprotein (VSV-G) or a nucleotide sequence encoding baboon endogenous virus envelope glycoprotein, which facilitates the formation of an envelope, enhances the virus infectivity, and enables the infections of wider range of host cells.

Preferably, the lentivirus packaging system further comprises one or more plasmids comprising a nucleotide sequence of vpu gene, a nucleotide sequence of nef gene, a nucleotide sequence of vif gene, or a nucleotide sequence of vpr gene.

Preferably, the transfer plasmid may further comprise a gene of interest to be delivered.

Preferably, the gene of interest to be delivered comprises a nucleotide sequence encoding an anti-CD19 receptor, and the anti-CD19 receptor is a receptor specifically binding to CD19 antigen.

According to the present invention, the nucleotide sequence encoding the anti-CD19 receptor is the nucleotide sequence encoding anti-CD19 receptor coupled with BBz disclosed in the article by Porter David L., et al. "Chimeric antigen receptor-modified T cells in chronic lymphoid leukemia." N engl j Med 365 (2011): 725-733, wherein BBz comprises a co-stimulatory domain from 4-1BB and a CD3ζ endodomain. The anti-CD19 receptor can be further used for preparing a chimeric antigen receptor (CAR) cell for the treatment of cancer. In one embodiment of the present invention, the nucleotide sequence encoding the anti-CD19 receptor comprises a nucleotide sequence encoding the anti-CD19 receptor coupled with BBz (CD19-BBz).

The present invention further provides a lentivirus, which is produced by the aforementioned lentivirus packaging system. Compared with the third-generation lentivirus packaging system, the produced lentivirus of the present invention further has TAT proteins in the virus particle, and has higher transduction efficiency than that of the third-generation lentivirus packaging system after tests.

The present invention further provides an isolated cell, which is obtained by transducing a gene of interest to a nucleated cell by the aforementioned lentivirus. Preferably, the nucleated cell comprises, but not limit to, an isolated T cell, an isolated natural killer cell, an isolated natural killer T cell or an isolated adipose stem cell. Accordingly, the isolated cell could be further used for preparing a chimeric antigen receptor cell for the treatment of cancer. In other words, the present invention further provides a use of an isolated cell for manufacturing a medicament for treatment of cancer or a method for treating cancer, comprising administering to a subject in need thereof a medicament comprising an effective amount of the isolated cell. The present invention further provides a method of increasing the yield of lentivirus in a host cell, comprising a step of transfecting the host cell with the lentivirus packaging system of the present invention.

Preferably, the host cell comprises a mammalian cell.

Preferably, the mammalian cell comprises the Human Embryonic Kidney 293 Cells (HEK293) or the 293T cell (HEK293T), wherein the 293T cell is the cell obtained through transfecting HEK293 cells with a gene of SV40 T antigen.

In one embodiment, the host cell is the 293T cell.

In one embodiment, the host cell is a pkr knockout 293T cell. The lentivirus packaging system of the present invention produces lentivirus in the pkr knockout 293T cell, which indeed can increase the virus titer of the produced lentivirus.

The lentivirus packaging system of the present invention can increase the virus titer of the produced lentivirus, and increase the transduction rate and gene delivery efficiency upon T cell transduction. Accordingly, the quality of gene modified cells will not be affected by the excessively low virus titer, which requires expanding the transduction volume and lowers the transduction efficiency. Therefore, the lentivirus packaging system of the present invention can significantly reduce the cost of gene modified cell products, such as the chimeric antigen receptor T cell (CAR-T) product.

DETAILED DESCRIPTION OF THE PREFERRED EMBODIMENTS

By taking reference to the drawings, the preparation examples and experimental examples, the technical means adopted by the present invention to achieve the desirable purpose of the invention are further illustrated as follows.

Figure 1:
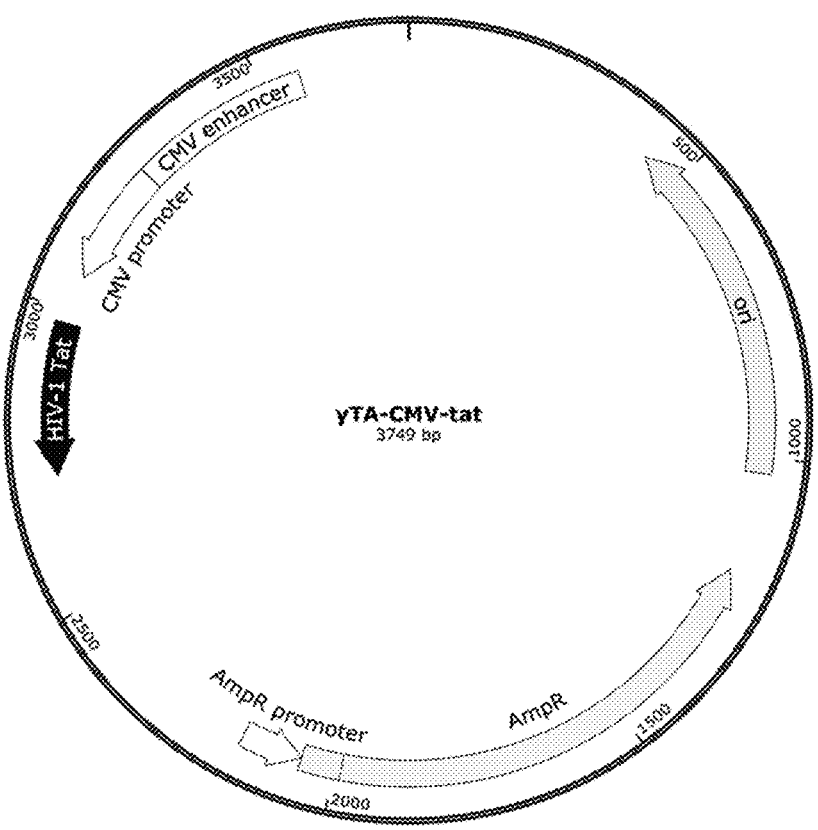
FIG. 1 is a schematic diagram of the expression vector of yTA-CMV-tat of the present invention.

Preparation Example 1 (PE1): Constructing the Packaging Plasmid Comprising a Gene of TAR RNA Binding Protein First, a DNA fragment containing the CMV promoter sequence prepared from pAll-Cas9-B2M_1-DP plasmid through the PspXI/AgeI restriction enzyme digestion was ligated into the XmaI/SalI linearized yTA-empty vector to obtain an yTA-CMV plasmid. Second, the nucleotide sequence encoding TAR RNA binding protein adopted in PE1 was a nucleotide sequence of tat gene without introns, i.e. that of SEQ ID NO: 1, which was prepared as follows: the DNA fragment containing the aforementioned SEQ ID NO: 1 sequence was amplified from the pCMVdeltaR8.91 plasmid (purchased from Academia Sinica RNAi Core facility), digested with NheI/BsrGI restriction enzyme, and then ligated with NheI/BsrGI linearized yTA-CMV plasmid to obtain the yTA-CMV-tat plasmid as shown in FIG. 1, which had 3749 bp. The aforementioned pAll-Cas9-B2M_1-DP plasmid was obtained through modifying the pAll-Cas9.Ppuro plasmid (purchased from Academia Sinica RNAi Core facility, Product No. C6-8-67) through replacing the DNA sequence between two BsmBI cutting sites with a B2M gRNA sequence and removing the anti-puromycin gene expressing cassette by using PCR amplification and SacII restriction enzyme digestion methods. The aforementioned XmaI/SalI linearized yTA-empty vector was prepared from an yTA-empty plasmid, which was obtained through removing the sequence between two SacII restriction enzyme sites of an yTA-WPRE_P plasmid. The yTA-WPRE_P plasmid was generated through inserting a nucleotide sequence involving the 1 to 507 nt of WPRE sequence amplified from the pAll-Cas9.Ppuro plasmid through PCR into the T&A™ Cloning Vector cloning vector (T&A™ Cloning Kit, FYC001-20P, YEASTERN BIOTECH).

Preparation Example 2 (PE2): Constructing the Transfer Plasmid Comprising CD19-BBz The hPGK promoter and PAC gene of pLAS5w.Ppuro plasmid comprising a nucleotide sequence of TAR-reserved chimeric 5'-LTR and driven by RSV promoter (purchased from Academia Sinica RNAi Core facility, Product No. C6-8-39) were deleted to obtain a pLAS5w plasmid, which was provided by Genscript. A nucleotide sequence encoding CD19-BBz from Lenti-EF1a-CD19 plasmid was inserted into BstBI/NheI linearized pLAS5w plasmid (prepared by Creative Biolabs). The aforementioned nucleotide sequence of TAR in TAR-reserved chimeric 5'-LTR was shown as SEQ ID NO: 2.

Experimental Example 1: Preparing Lentivirus

The 293T cells were cultured in the Dulbecco's Modified Eagle Medium (DMEM) (Gibco, 11965-092) containing 10% Fetal Bovine Serum (FBS) at 37° C. under 5% $CO_2$ for 3 days in a T875 culture flask (large scale) with an original cell number of $1.5 \times 10^7$ cells and in 10 cm culture dish (small scale) with an original cell number of $1 \times 10^6$ cells. Then, the 293T cells were transfected in DMEM containing 10% FBS by using PolyJet™ transfection reagent (SignaGen Laboratories) and plasmids of the second-generation lentivirus packaging system serving as Comparative Example 1 (CE1), the third-generation lentivirus packaging system serving as Comparative Example 2 (CE2), or the lentivirus packaging system of the present invention serving as Example 1 or 2 (E1 or E2). The weight ratios between the packaging plasmids in E1 and E2 are different. The lentivirus of CE2 and E1 were prepared both in a large scale and a small scale. The lentivirus of CE1 and E2 were only prepared in a small scale. The aforementioned operation was in accordance with the operation manual of PolyJet™ transfection reagent. The second-generation lentivirus packaging system (purchased from Academia Sinica RNAi Core facility) in CE1 and the third-generation lentivirus packaging system (purchased from Aldevron) in CE2 were known technology. The next day, the culture medium of Opti-MEM (51985-034, Gibco) was substituted for DMEM containing 10% FBS, and was harvested for the first time after 24 hours to obtain a supernatant containing lentivirus particles. Fresh Opti-MEM medium was supplemented for culturing for another 24 hours and was harvested for the second time to obtain another supernatant containing lentivirus particles. After all harvesting processes were completed, all supernatants containing lentivirus particles were mixed together, and the total volume was then concentrated 100-fold by using Lenti-X Concentrator (Takara Bio).

TABLE 1 the plasmid combinations of the packaging system for preparing lentivirus

Figure 2A:
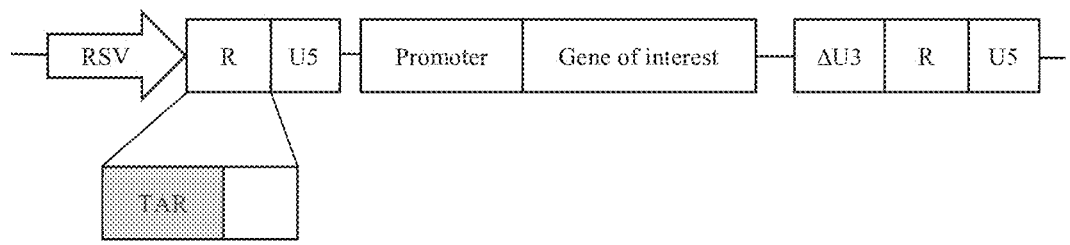
FIG. 2A is a schematic diagram of the transfer plasmid comprising TAR-reserved chimeric 5'-LTR of the lentivirus packaging system in Example 1 (E1, Table 1).
Figure 2B:
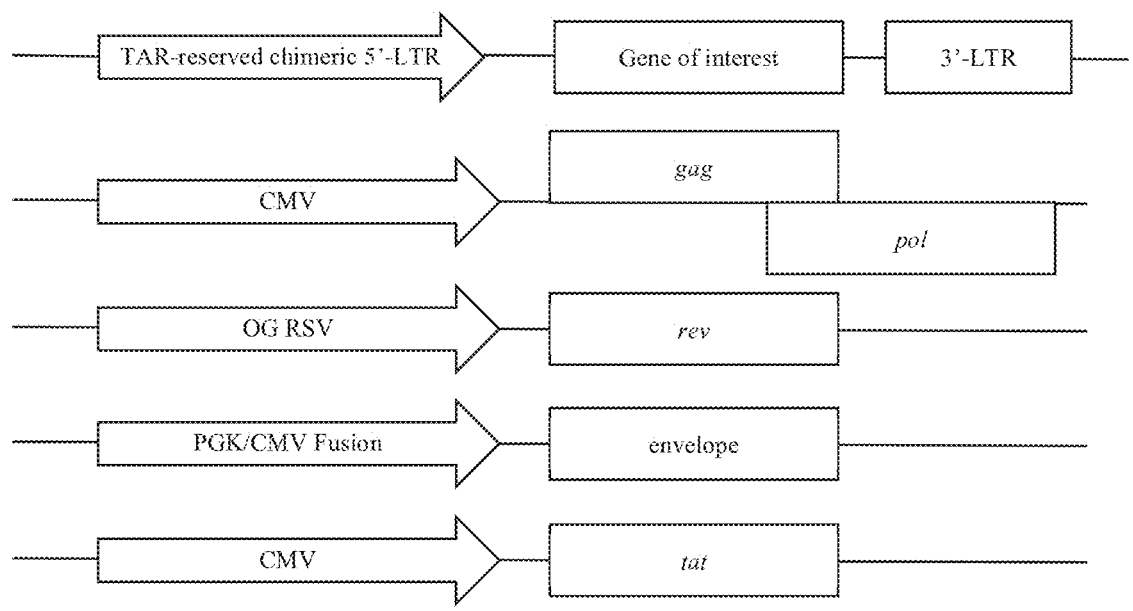
FIG. 2B is a schematic diagram of the plasmid combination of the lentivirus packaging system in Example 1 (E1, Table 1).

| Packaging system | Plasmids | 10 cm culture dish (small scale) | | T875 culture flask (large scale) | |
|---|---|---|---|---|---|
| | | Amount (µg) | Total amount (µg) | Amount (µg) | Total amount (µg) |
| The second-generation lentivirus packaging system (CE1) | The transfer plasmid comprising CD19-BBz (driven by RSV promoter) recited in PE2 | 2.5 | 5 | N/A | N/A |
| | pCMV deltaR8.91 (purchased from Academia Sinica RNAi Core facility) | 2.25 | | N/A | N/A |
| | pMD.G (purchased from Academia Sinica RNAi Core facility) | 0.25 | | N/A | N/A |
| The third-generation lentivirus packaging system (CE2) | The transfer plasmid comprising CD19-BBz recited in PE2 | 2.5 | 8 | 50 | 160 |
| | The plasmid comprising a nucleotide sequence of gag gene and a nucleotide sequence of pol gene (driven by CMV promoter) (purchased from Aldevron, pALD-Lenti (Ampicillin resistance)) | 2.5 | | 50 | |
| | The plasmid comprising a nucleotide sequence of rev gene (driven by OG-RSV promoter) (purchased from Aldevron, pALD-Lenti (Ampicillin resistance)) | 1 | | 20 | |
| | The envelope plasmid comprising a nucleotide sequence encoding VSV-G (driven by PGK/CMV Fusion promoter) (purchased from Aldevron, pALD-Lenti (Ampicillin resistance)) | 2 | | 40 | |
| E1: the lentivirus packaging system of the present invention (As shown in FIG. 2B) | The transfer plasmid comprising CD19-BBz recited in PE2 (As shown in FIG. 2A, LTR is segmented into the U3, R and U5 regions, wherein the R region has TAR sequence (TAR-reserved), and ΔU3 refers to the truncated U3 region. | 2.5 | 9 | 50 | 180 |
| | The plasmid comprising a nucleotide sequence of gag gene and a nucleotide sequence of pol gene (driven by CMV promoter) (purchased from Aldevron, pALD-Lenti (Ampicillin resistance)) | 2.5 | | 50 | |
| | The plasmid of yTA-CMV-tat of PE1 (driven by CMV promoter) | 1 | | 20 | |
| | The plasmid comprising a nucleotide sequence of rev gene (driven by OG-RSV promoter) (purchased from | 1 | | 20 | |

TABLE 1-continued the plasmid combinations of the packaging system for preparing lentivirus

| Packaging system | Plasmids | 10 cm culture dish (small scale) | | T875 culture flask (large scale) | |
|---|---|---|---|---|---|
| | | Amount (μg) | Total amount (μg) | Amount (μg) | Total amount (μg) |
| | Aldevron, pALD-Lenti (Ampicillin resistance)) The envelope plasmid comprising a nucleotide sequence encoding VSV-G (driven by PGK/CMV Fusion promoter) (purchased from Aldevron, pALD-Lenti (Ampicillin resistance)) | 2 | | 40 | |
| E2: The lentivirus packaging system of the present invention | The transfer plasmid comprising CD19-BBz recited in PE2 | 4 | 9.2 | N/A | N/A |
| | The plasmid comprising a nucleotide sequence of gag gene and a nucleotide sequence of pol gene (driven by CMV promoter) (purchased from Aldevron, pALD-Lenti (Ampicillin resistance)) | 2.4 | | N/A | N/A |
| | The plasmid of yTA-CMV-tat of PE1 (driven by CMV promoter) | 1.2 | | N/A | N/A |
| | The plasmid comprising a nucleotide sequence of rev gene (driven by OG-RSV promoter) (purchased from Aldevron, pALD-Lenti (Ampicillin resistance)) | 1.2 | | N/A | N/A |
| | The envelope plasmid comprising a nucleotide sequence encoding VSV-G (driven by PGK/CMV Fusion promoter) (purchased from Aldevron, pALD-Lenti (Ampicillin resistance)) | 0.4 | | N/A | N/A |

The lentivirus prepared in Experimental Example 1 was tested to determine lentivirus titer. Specifically, the lentivirus titer was determined by the result of Jurkat cells transducing with 3-fold serial diluted (3-fold to 6561-fold) virus samples. First, 50 μL of lentivirus sample was added to 100 μL of X-Vivo 15 medium, and a 3-fold serial dilution was carried out until the 6561-fold diluted sample was obtained. Second, 100 μL of $4\times10^5$ cells/ml Jurkat cells suspended in a culture medium (RPMI 1640 medium (11875, Gibco) containing 10% FBS) were mixed with 50 μL of each serial diluted lentivirus sample in a 96-well plate (U-Shaped-Bottom) on Day 0. On Day 2, another 100 μL of fresh culture medium was added to each well, and the 96-well cell culture plate was incubated in the culture incubator for another 24 hours. Afterwards, an antibody of biotin-conjugated goat anti-mouse IgG F(ab)$_2$ fragment (Jackson ImmunoResearch) and Streptavidin-PE (Invitrogen) was used to detect CD19-BBz, and the flow cytometer was used to analyze the percentage of cells expressing the target protein (CD19-BBz) to determine the virus transduction efficacy. The functional virus titer was calculated as follows:

Virus titer (TU/ml)=(percentage of the cells expressing CD19-BBz/100)×4×10$^4$×20×dilution-fold.

Figure 3:
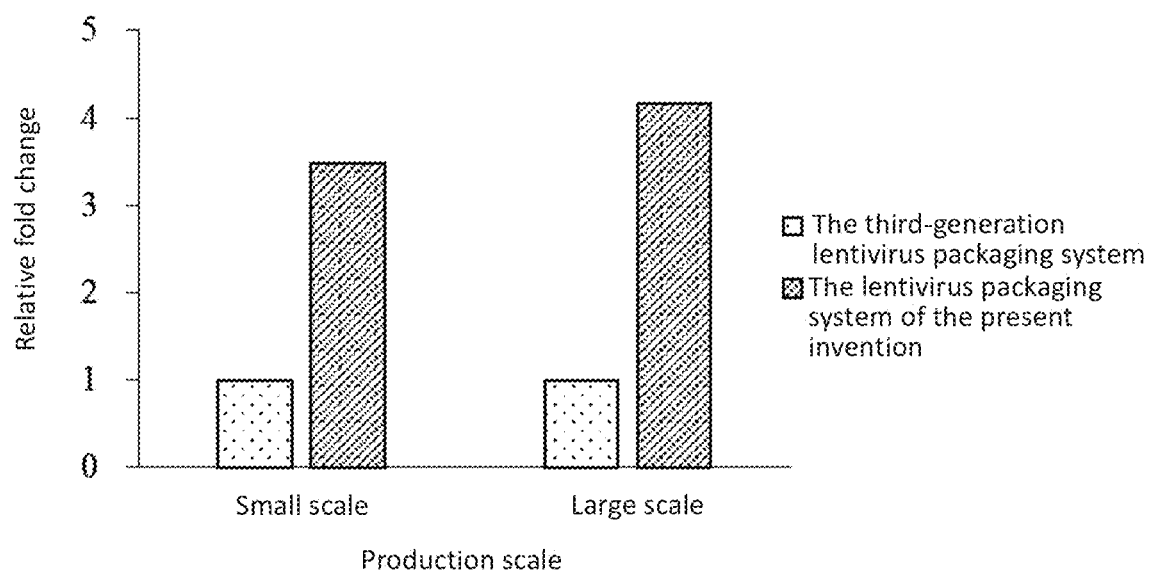
FIG. 3 is a bar chart showing the relative fold change of lentivirus titer of the lentivirus obtained by the lentivirus packaging system of the present invention (E1, Table 1) produced in a large scale and a small scale in comparison with each of that corresponding to the third-generation lentivirus packaging system (CE2, Table 1).

When the lentivirus prepared by the lentivirus packaging system of the present invention (E2, Table 1) was examined, and the percentage of CD19-BBz positive population of the 729-fold diluted sample was used, in which the percentage of the cells expressing CD19-BBz was 16.09%, the virus titer obtained was $9.38\times10^7$ transducing units (TU)/ml. Furthermore, the virus titer of the lentivirus prepared by using E2 was better than that prepared by using E1. Besides, as shown in FIG. 3, regardless of small scale or large scale production, the CD19-BBz lentivirus produced by the lentivirus packaging system of the present invention (E1) had a virus titer that was significantly better than that of the third-generation lentivirus packaging system (CE2), wherein the virus titers of E1 were 3.48-fold and 4.16-fold higher than that of the third-generation lentivirus packaging system (CE2) in small scale and large scale production, respectively. Furthermore, the virus titer was multiplied by the virus volume to obtain a lentivirus yield. As the volumes of virus products of Examples and Comparative Examples were the same, the yields of the CD19-BBz lentivirus produced by the lentivirus packaging system of the present invention (E1) were also 3.48-fold and 4.16-fold higher than that of the third-generation lentivirus packaging system (CE2) in small scale and large scale production, respectively. Therefore, the virus yield by using the lentivirus packaging system of the present invention was significantly better than that of the third-generation lentivirus packaging system (CE2). Accordingly, the adoption of the lentivirus packaging system of the present invention, regardless of small scale or large scale production, indeed increases the yield of lentivirus owing to the co-expression of TAT protein, and shows more advantages than the third-generation lentivirus packaging system (CE2).

Preparation Example 3 (PE3): Preparing the Pkr Knockout 293T Cells

Figure 4:
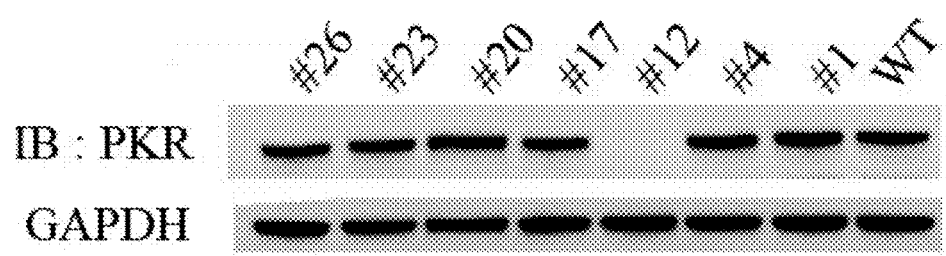
FIG. 4 is a western blot result showing the expression level of PKR protein of the tested cell strains in Preparation Example 3.

Two partial complementary primers were annealed to prepare a PKR guide RNA (gRNA) which was 24 bp, and then ligated into a BsmBI linearized Cas9-T2A-eGFP-DP plasmid to obtain the Cas9-PKR-T2A-eGFP-DP all-in-one plasmid. The sequence of PKR gRNA is GCAACCUAC-CUCCUAUCAUG (SEQ ID NO: 3), and CRISPR/Cas9 gene editing technique was applied to prepare the pkr knockout 293T cells, wherein said pkr means Protein kinase R (PKR), also named Eukaryotic translation initiation factor 2-alpha kinase 2 (eIF2AK2). Specifically, the Cas9-PKR-T2A-eGFP-DP all-in-one plasmid containing said gRNA sequence was transfected into 293T cells through calcium-phosphate method. The individual candidate clone was obtained through seeding the transfected 293T cells to a 96-well plate with a cell density of 0.5 cell/well, and examined by western blot, which comprised steps as follows. The total proteins of each individual candidate clones were prepared by using RIPA lysis buffer, and then analyzed for PKR protein expression by using the rabbit anti-PKR polyclonal antibody (GTX132826, GeneTex). The GAPDH protein served as internal control, and wild type 293T cells served as a control group. The 293T cell strains #1, #4, #12, #17, #20, #23 and #26 were selected from the 96-well plate, and the western blot result (See FIG. 4) indicated that the pkr gene in the 293T cell strain #12 was successfully knocked out and the 293T cell strain #12 was further used to prepare lentivirus in Experimental Example 2.

Experimental Example 2: Preparing Lentivirus by the Pkr Knockout 293T Cells

Figure 5:
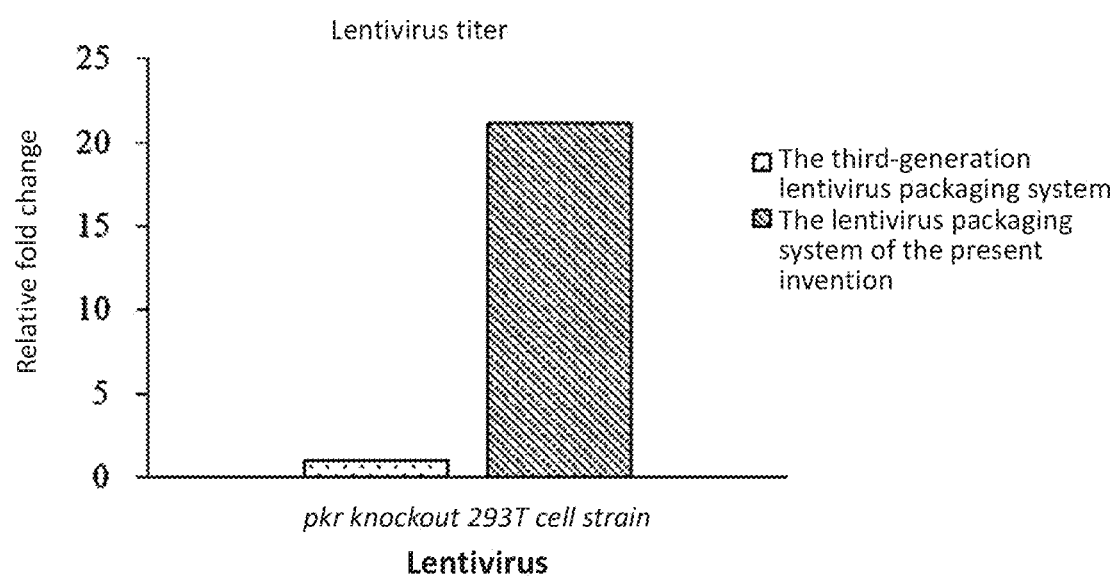
FIG. 5 is a bar chart showing the relative fold change of lentivirus titer of the lentivirus produced from the pkr knockout 293T cells transfected with the third-generation packaging system (CE2, Table 1) and the lentivirus packaging system of the present invention (E1, Table 1) in small scale.

The lentivirus production method of Experimental Example 2 is similar to that of Experimental Example 1 except for the host cell. The lentivirus were produced by transfecting the pkr knockout 293T #12 cell, obtained from PE3, with plasmids of the third-generation packaging system (CE2, Table 1) or the packaging system of the present invention (E1, Table 1) by using PolyJet™ in 10-cm culture dishes (small scale). The virus titer was determined by the virus titration steps described in PE2. The results were shown in FIG. 5 and indicated that the virus titer of the lentivirus prepared by using the plasmid combination of the lentivirus packaging system of the present invention (E1, Table 1) was 22.2-fold higher than that by using the third-generation lentivirus packaging system (CE2, Table 1). Therefore, the adoption of the pkr knockout 293T cells for producing lentivirus indeed significantly increased the virus titer of the lentivirus produced by the plasmid combination of the lentivirus packaging system of the present invention.

Experimental Example 3: Infection Ability Test by Transducing Primary T Cell

Primary T cells were purified and activated from Ficoll (GE)-prepared peripheral blood mononuclear cells (PBMC) of healthy donors by using CD3/CD28 expander beads (Thermo Fisher Scientific). On the next day (Transduction-Day 1), these purified T cells were respectively transduced with the lentivirus prepared in a small scale by using the second-generation lentivirus packaging system, the third-generation lentivirus packaging system and the lentivirus packaging system of the present invention recited in Experimental Example 1. The steps were summarized as follows: 1 mL of primary T cells with the cell number of $1\times10^6$ were co-cultured with the lentivirus prepared in Experimental Example 1, with virus dosage of Multiplicity of Infection (MOI) 1, 3 and 5. After transduction for two days (Transduction-Day 3), CD3/CD28 expander beads were removed. Finally, the percentage of the primary T cells expressing the gene of interest (CD19-BBz) was examined by using flow cytometry on Transduction-Day 6. Specifically, $1\times10^5$ primary T cells were collected and suspended in 100 μL staining solution, which is a PBS solution containing 1% Fetal Calf Serum (FCS). The staining solution containing the primary T cells was added with a primary antibody (Biotin-conjugated goat anti mouse IgG F(ab)$_2$) and stood still at room temperature for 20 minutes. The primary T cells were washed with 1 mL staining solution for two times, and then re-suspended with 100 μL staining solution containing Streptavidin-PE. After incubating at room temperature for another 20 minutes, the stained primary T cells were washed with 1 mL staining solution for two times, re-suspended in a suitable amount of staining solution, and analyzed by the flow cytometry.

Figure 6A:
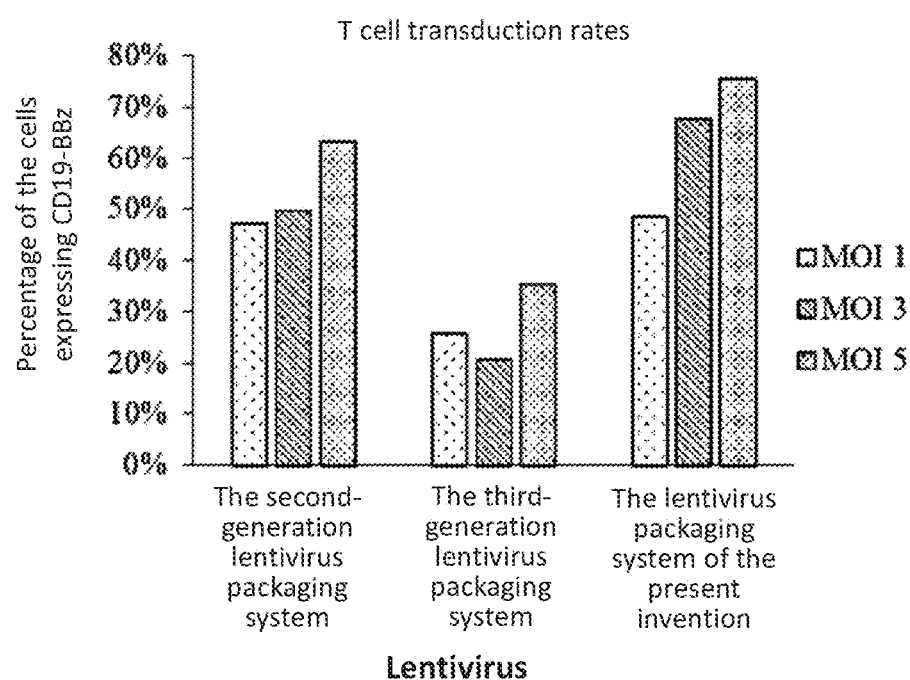
FIG. 6A is a bar chart showing the T cell transduction rates of the lentivirus produced by the second generation (CE1, Table 1), the third generation (CE2, Table 1) and the lentivirus packaging system of the present invention (E1, Table 1).
Figure 6B:
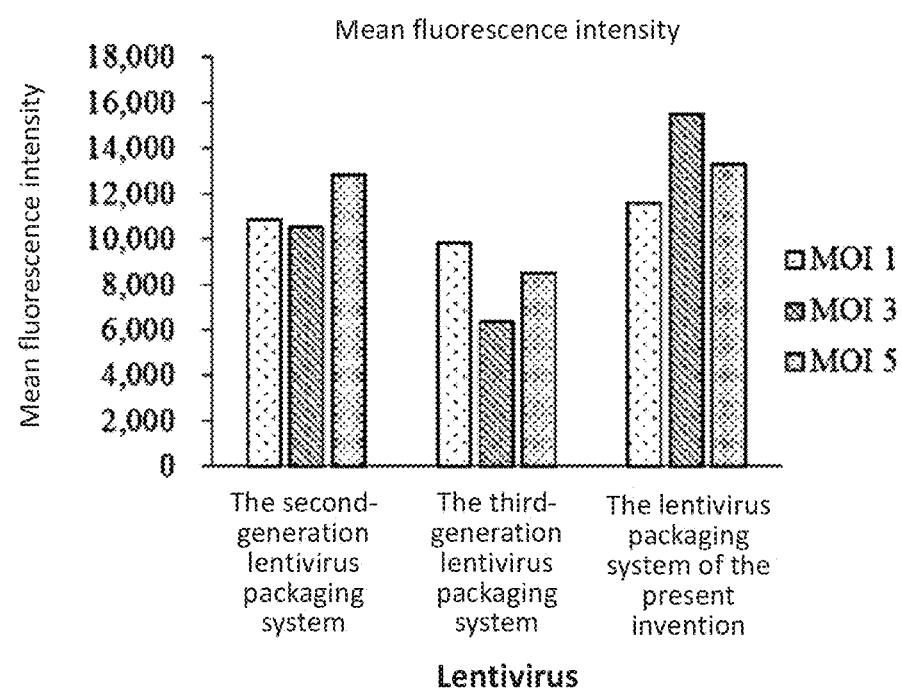
FIG. 6B is a bar chart showing the mean fluorescence intensity in the T cells transduced with the lentivirus produced by the second generation, the third generation and the lentivirus packaging system of the present invention.
Figure 6C:
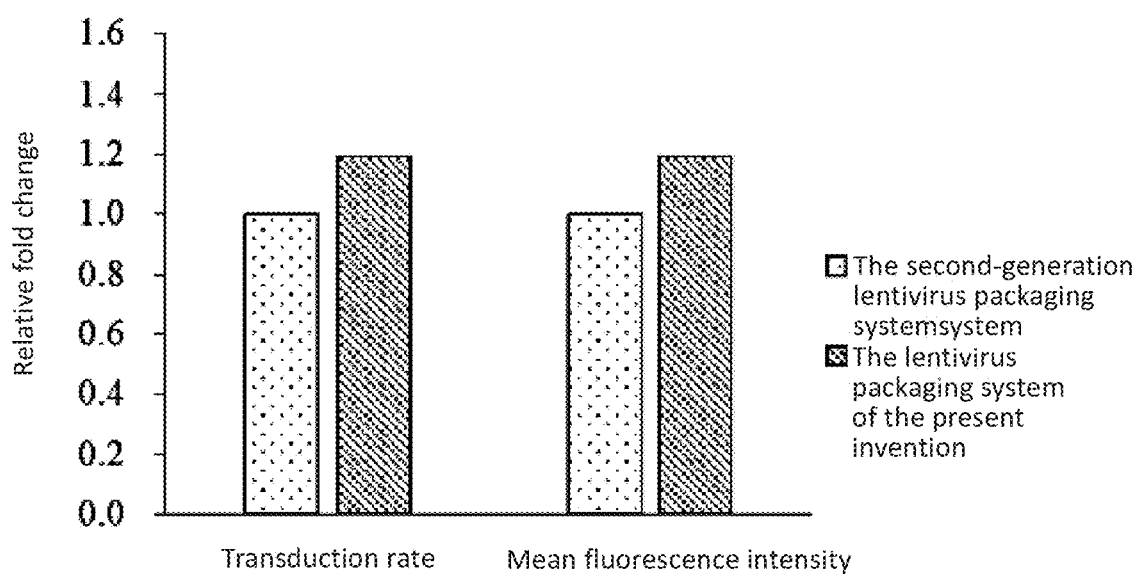
FIG. 6C is a bar chart showing the relative fold change of both the transduction rate and the mean fluorescence intensity of the T cells transduced with the lentivirus produced by the lentivirus packaging system of the present invention (E1, Table 1) in comparison with those of the second-generation lentivirus packaging system (CE1, Table 1).

The analysis results of the flow cytometry were shown in FIG. 6A to FIG. 6C. In FIG. 6A, in all three different MOI groups, the T cells transduced by the lentivirus prepared by the lentivirus packaging system of the present invention (E1) showed higher percentage of CD19-BBz expressing cells than that of the second or third-generations lentivirus packaging system. Therefore, in comparison with the second- and third-generation lentivirus packaging systems, the lentivirus prepared by the lentivirus packaging system of the present invention has the best transduction rate, transduction efficiency and gene delivery efficacy. In FIG. 6B, in all three different MOI groups, the mean fluorescence intensity of T cells transduced with the lentivirus prepared by the lentivirus packaging system of the present invention (E1) was also higher than that of the second- or third-generation lentivirus packaging system. In FIG. 6C, the T cells transduced by the lentivirus prepared by using the lentivirus packaging system of the present invention (E1) showed better transduction rate and mean fluorescence intensity, which were 1.2-fold higher than those of the second-generation lentivirus packaging system, wherein said 1.2-fold was the average of the relative fold change in the groups of MOI 1, 3 and 5. Therefore, the lentivirus packaging system of the present invention can increase the activity of the lentivirus produced thereby.

Accordingly, the lentivirus packaging system of the present invention can significantly increase the yield and activity of lentivirus, and effectively increase the gene delivery efficiency during genetic modifications of cells, so that the cost of gene modified cells can be reduced. In addition, the pkr knockout 293T cells can further be used to enhance the yield of the lentivirus produced therefrom.

The aforementioned detailed description simply recites preferred embodiments and is by no means to restrict the present invention in any aspect. Although the present invention has been disclosed as the aforementioned preferred embodiments, the inventor does not mean to restrict the present invention accordingly. Without departing from the range of the technical solutions of the present invention, any person having ordinary skill in the art can take advantages of the aforementioned technical content and conduct some adjustments or modifications to obtain embodiments with equivalent variations and efficacies. Without deviating from the content of the technical solutions of the present invention, the simple adjustments, equivalent variations and modifications carried out for the aforementioned embodiments and based on the substantial technique of the present invention still fall within the range of the technical solutions of the present invention.

What is claimed is:

1. A lentivirus packaging system, comprising:
   a transfer plasmid comprising a nucleotide sequence of a trans-activation response (TAR) element-reserved chimeric 5' long terminal repeat (TAR-reserved chimeric 5'-LTR);
   a first packaging plasmid comprising a CMV promoter, a nucleotide sequence of a gag gene and a nucleotide sequence of a pol gene;
   a second packaging plasmid comprising a CMV promoter, a nucleotide sequence of a tat gene;
   a third packaging plasmid comprising an OG-RSV promoter, a nucleotide sequence of a rev gene; and
   an envelope plasmid,
   wherein a weight ratio of the transfer plasmid, the first packaging plasmid, the second packaging plasmid, the third packaging plasmid and the envelope plasmid is 3 to 12:3 to 7:1 to 4:1 to 4:0.8 to 6, respectively.

2. The lentivirus packaging system as claimed in claim 1, wherein the nucleotide sequence of the tat gene comprises the nucleotide sequence of SEQ ID NO: 1.

3. The lentivirus packaging system as claimed in claim 1, wherein the envelope plasmid comprises a nucleotide sequence encoding a vesicular stomatitis virus glycoprotein (VSV-G) or a nucleotide sequence encoding a baboon endogenous virus envelope.

4. The lentivirus packaging system as claimed in claim 1, wherein the nucleotide sequence of the TAR-reserved chimeric 5'-LTR has a nucleotide sequence of a TAR, and the nucleotide sequence of the TAR comprises the nucleotide sequence of SEQ ID NO: 2.

5. A method of increasing the yield of lentivirus in a host cell, comprising a step of using the lentivirus packaging system as claimed in claim 1 to transfect the host cell, wherein the host cell is a pkr knockout 293T cell.

6. A method of increasing the yield of lentivirus in a host cell, comprising a step of using the lentivirus packaging system as claimed in claim 1 to transfect the host cell.

7. The method of increasing the yield of lentivirus in the host cell as claimed in claim 6, wherein the host cell comprises a mammalian cell.

8. The method of increasing the yield of lentivirus in the host cell as claimed in claim 7, wherein the mammalian cell comprises a Human Embryonic Kidney 293 cell (HEK293) or a 293T cell (HEK293T).

9. An isolated cell transfected with the lentivirus packaging system as claimed in claim 1.

* * * * *